US009557284B2

(12) United States Patent
Vogler (10) Patent No.: US 9,557,284 B2
(45) Date of Patent: Jan. 31, 2017

(54) SCANNING ILLUMINATING DEVICE, IMAGING DEVICE COMPRISING SAME AND METHOD OF IMPLEMENTATION (71) Applicant: Commissariat A L'Energie Atomique et Aux Energies Alternatives, Paris (FR)

(72) Inventor: Rene Vogler, Vitry-sur-Seine (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 44 days.

(21) Appl. No.: 14/653,001

(22) PCT Filed: Dec. 18, 2013

(86) PCT No.: PCT/FR2013/053167
§ 371 (c)(1),
(2) Date: Aug. 18, 2015

(87) PCT Pub. No.: WO2014/096705
PCT Pub. Date: Jun. 26, 2014

(65) Prior Publication Data
US 2015/0346120 A1    Dec. 3, 2015

(30) Foreign Application Priority Data

Dec. 20, 2012 (FR) ...................... 12 62475

(51) Int. Cl.
*G01N 23/203* (2006.01)
*H04N 5/32* (2006.01)
(Continued)

(52) U.S. Cl.
CPC ............ *G01N 23/203* (2013.01); *G01N 21/47* (2013.01); *G01N 21/59* (2013.01); *G01N 23/04* (2013.01);
(Continued)

(58) Field of Classification Search
CPC ...... G01N 23/203; G01N 21/47; G01N 21/59; G01N 23/04; G21K 1/02; H04N 5/32; H04N 5/33
See application file for complete search history.

(56) References Cited

U.S. PATENT DOCUMENTS 6,434,219 B1    8/2002 Rothschild et al.
2006/0245548 A1    11/2006 Callerame et al.
(Continued)

FOREIGN PATENT DOCUMENTS

CN    1246647 A    3/2000
EP    2520927 A1    11/2012

*Primary Examiner* — David Porta
*Assistant Examiner* — Mindy Vu
(74) *Attorney, Agent, or Firm* — Brinks Gilson & Lione (57) ABSTRACT

A scanning illuminating device includes an emission center from which radiation is emitted in an illuminating sector. A cylindrical ring is centered on the source and is rotatably movable about a first axis. The ring includes a plurality of slits regularly distributed about its axis of rotation and having the same angular amplitude α. A cylinder portion is centered on the source and is rotatably movable about a second axis crossing the first axis at the center and forming a nonzero angle therewith. The cylinder portion includes a slit having an angular amplitude β. A first device control of the rotation of the ring, defining an elementary angular step as such that an integer N1 other than 1 meets the condition $\alpha = N1 \cdot \alpha\alpha$. A second device controls the rotation of the ring portion defining an angular step $\beta\beta$ such that an integer N2 other than 1 meets the condition $\beta = N2 \cdot \beta\beta$.

20 Claims, 5 Drawing Sheets (51) Int. Cl.

| | | |
|---|---|---|
| *H04N 5/33* | (2006.01) | |
| *G01N 23/04* | (2006.01) | |
| *G21K 1/02* | (2006.01) | |
| *G01N 21/59* | (2006.01) | |
| *G01N 21/47* | (2006.01) | |
| *G21K 1/04* | (2006.01) | |

(52) U.S. Cl.
CPC  *G21K 1/02* (2013.01); *H04N 5/32* (2013.01); *H04N 5/33* (2013.01); *G01N 2201/104* (2013.01); *G01N 2223/314* (2013.01); *G01N 2223/3301* (2013.01); *G01N 2223/335* (2013.01); *G21K 1/043* (2013.01)

(56) References Cited

U.S. PATENT DOCUMENTS

| | | | |
|---|---|---|---|
| 2008/0142719 A1 | 6/2008 | Hugg et al. | |
| 2010/0045956 A1* | 2/2010 | Van De Kerkhof | G01M 11/0264 355/71 |
| 2010/0296624 A1* | 11/2010 | Bontus | A61B 6/032 378/4 |
| 2012/0133888 A1* | 5/2012 | Gray | A61B 3/1025 351/206 |

* cited by examiner

SCANNING ILLUMINATING DEVICE, IMAGING DEVICE COMPRISING SAME AND METHOD OF IMPLEMENTATION

RELATED APPLICATIONS

This application is a U.S. nationalization of PCT application No. PCT/FR2013/053167, filed Dec. 18, 2013 and published as PCT publication No. WO2014/096705 on Jun. 26, 2014, the disclosure of which is incorporated by reference herein.

TECHNICAL FIELD

The invention concerns a scanning illuminating device, called a radiation modulator, an imaging device using such a modulator and a method of implementing such a modulator.

BACKGROUND

Imaging consists in illuminating an object using a source of radiation, often of high energy, and of forming an image on the basis of the radiation that is back-scattered (especially in the case of objects opaque to the radiation) or transmitted. The radiation considered here is for example radiation that penetrates the material, typically X-rays, or even "gamma" rays, but may also be what is referred to as THz radiation, that is to say radiation of which the frequency, of the order of the terahertz, situates it between the infrared and the microwave domain. These concepts of illumination or imaging do not in any way imply that the radiation is in the visible domain (generally it is the opposite case); the term irradiation is sometimes used, in the case of certain penetrating radiation.

There are two broad families of imaging devices according to the illumination configuration used:

Imaging devices with "imager", in which the source fully and uniformly illuminates the object; the detection of the back-scattered radiation is carried out by a pixelated imager of large format associated with an image forming system of greater or lesser complexity, "Scanning" devices in which the source illuminates part (in practice a small zone) of the object at a given time and performs scanning in order to cover the whole of that object during a scanning cycle. Collimation is generally placed in front of the source in order to reduce the angular amplitude of the illumination beam at each instant and thus the illuminated zone. The back-scattered radiation (and/or the transmitted radiation) is collected by one or more one-dimensional detectors synchronized with the scanning by the source.

There are a wide variety of imaging devices with imager.

There are thus imaging devices with a virtual imager (reconstitution by scanning of the field of view of a detector, in practice one-dimensional, which is strongly collimated, and of which movement is provided using Cartesian or polar coordinates), and imaging devices with a matrix imager (this matrix imager is formed from a matrix of strongly collimated one-dimensional detectors). Developed before the appearance of large detection matrices, they are still used in in vitro scintigraphy and for the examination of small laboratory animals. These devices lack spatial resolution given the size of the unit detector and the collimation used to form the image.

Imaging devices with imager were then developed thanks to the appearance of pixelated imagers; a particularly simple version is the pinhole imager, that is to say it employs a hole of small size formed in a screen interposed between the illuminated object and the detector. The spatial resolution increases when the size of the hole reduces such that the main drawback of this type of imager is that an increase in spatial resolution implies a reduction in the quantity of radiation transmitted by the pinhole; this leads either to very long exposure times, or to images of poor signal-to-noise ratio.

To improve the signal-to-noise ratio, it is possible to use the technique of penumbra imaging, in which the pinhole is replaced by an aperture of greater size (in the shape of a disk, or in a ring, for example). The quantity of radiation received by the detector is higher but the image is blurred and must be deconvoluted by mathematical processing using the knowledge of the aperture shape and of the detection geometry to determine the deconvolution kernel.

A second way to get around the limitations of the pinhole principle is the coded aperture technique, consisting of having multiple pinholes within the same screen, also called a mask; the quantity of radiation reaching the detector increases with the number of apertures. A reconstruction operation must then be carried out to reconstitute the image of the object. The distribution of the pinholes within a given mask must satisfy a certain number of rules to facilitate that reconstruction of the image and minimize the contribution of the noise.

The principle of the method has been described by: E. Fenimore and T. M. Cannon "Coded aperture imaging with uniformly redundant arrays", Applied Optics, Vol. 17, No. 3, p. 337-347, Jan. 2, 1978; several patents disclose devices implementing this coded aperture technique:

U.S. Pat. No. 4,389,633 (Fenimore et al) published in 1983,
PCT Pub. No. WO 97/45755 published in 1997,
PCT Pub. No. WO 02/13517 published in 2002,
PCT Pub. No. WO 02/056055 published in 2002,
U.S. Pat. Pub. No. 2004/218714 published in 2004 and
PCT Pub. No. WO 2007/091038 published in 2007, The main limitations of the coded aperture devices are their high cost since the large-size masks are costly to produce while the associated imagers must have dimensions at least equal to those of the mask. Their spatial resolution is not adjustable since it is linked, in particular, to the size of the holes in the mask and to the detection geometry.

An original device, described in PCT Pub. No. WO 2007/015784, consists of using X-ray focusing optics of very particular form enabling the radiation scattered by the object to be focused onto an imager of small size; however, the X-focusing optics do not operate for all radiation energies and its efficiency is rather low.

The other category of imagers, referred to as "scanning" imagers, also comprises several variants.

Thus, the simplest version consists of illuminating the object with a radiation beam (typically X-rays) of very small diameter (the term "pencil beam" is sometimes used) and of scanning the entire object by virtue of a mechanical system; the dimension of the radiation beam and the scanning step size determine the spatial resolution; such scanning is typically carried out by means of an annular ring movable around its center, pierced with collimation passages, the source of radiation being fixed, situated at the center of this annular wall; this ring may be of greater or lesser thickness depending on whether it is a wall pierced with holes or a disc holed in its center, in which radial channels are formed; this ring is sometimes called a chopper wheel. The rotation of this ring causes scanning of the beam perpendicularly to the rotational axis of the ring; the other movement ensuring the scanning of the object is conventionally provided by a movement of the object parallel to the rotational axis of the ring. A detector is placed beside the source; it records a series of signals which are then provided in matrix form to constitute the back-scattered image of the object.

Such a configuration, and examples of application are in particular described in U.S. Pat. No. 5,764,683, and PCT pub. Nos. WO 00/33060, WO 01/94984, WO 2004/043740 or WO 2006/102274.

According to a variant, the pencil beam results from the interception of a fan beam which is intercepted by a wheel of which the axis is parallel to the plane of the beam and which comprises radial slits; such a configuration and examples of application are in particular described in U.S. patents Re 28 544, U.S. Pat. No. 4,031,545, U.S. Pat. No. 4,799,247, U.S. Pat. No. 5,179,581, U.S. Pat. No. 5,181,234 or U.S. Pat. No. 6,094,472.

Instead of providing scanning by movement of a pencil beam in two transverse directions, it is also possible to generate a fan beam which is passed through by the object to observe, as is for example described in PCT pub. No. WO 98/20366. It is to be noted that the reconstruction of an image based on such scanning may involve coding similar to that indicated above in connection with the imaging devices with imager.

Variants implement both types of aforementioned scanning devices (by a pencil beam and by a fan beam), as is proposed by the PCT pub. Nos. WO 99/39189 and WO 2008/021807.

The devices described above serve in practice for the inspection of parcels, baggage, even freight trucks or people.

The drawback of this scanning configuration is in practice to use only a very small part of the radiation emitted by the source since the spatial resolution improves the finer the illumination beam; the source must therefore be of high intensity and the detection surface of large size if acquisition times of reasonable length are desired.

An increase in the quantity of radiation used may be obtained by increasing the number of beams; this may be provided by the coding of a localized source with absorbent masks comprising holes; it is then necessary to reconstruct the image by matrix inversion techniques. A simple version (with a plurality of pencil beams simultaneously formed by means of a chopper wheel, combined with movement of the object) is described in PCT pub. No. WO 01/94894. To obtain a good result, in particular when the scanning is provided in two transverse directions, the collimation holes forming the beams must satisfy disposition rules; the best-known principle consists of projecting masks and their opposites constituting the elements of a Hadamard matrix; this imaging method requires little computation power (it is a simple matrix multiplication) but its practical implementation is very complex. Typically, for an image of size N×N, it is necessary to project $2 \cdot N^2$ masks. The resolution of the final image depends on the size of the smallest projected pattern; the more it is sought to have details in that image, the higher the number of masks to project has to be; mechanically these masks must be produced and positioned with high precision; such a system is extremely complex and costly (see PCT pub. No. WO 2008/127385 published in 2008).

Another approach consists of performing coding in relation to an area source, with a pinhole to project the pattern onto the object. In the same way as previously, it is necessary to have a succession of different patterns to acquire the data then reconstruct the back-scattered image (cf. U.S. Pat. No. 6,950,495 published in 2005).

These coding devices are extremely complex since a source of large area must be produced with zones (pixel) that can be modulated individually for emission; furthermore, the emitted intensity must be sufficiently high to enable the projection of the patterns via a pinhole, which considerably attenuates the signal; as previously, the resolution depends on the size of the smallest projected pattern.

Thus, the known solutions implement scanning illuminating devices which are generally voluminous and complex from the mechanical point of view, particularly as the scanning in two perpendicular directions in practice requires movement of the object relative to the radiation source. Furthermore, these scanning illuminating devices in practice enable a high spatial resolution to be obtained only provided a beam of small dimensions only is applied to the object.

SUMMARY

The invention aims to mitigate the drawbacks of the known solutions and to provide, in a compact volume, illumination by scanning in two directions, while enabling the formation of images with a resolution which is not dictated by the scanning beam. Preferably, it is directed to enabling the scanning to be made by absorbing the radiation emitted by the source in a manner that is variable over time and in space; thus, preferably, it is directed to enabling the illumination to be made according to first provisions, for example for the purpose of taking a crude image, then according to other provisions enabling an image of better quality to be taken, possibly limited to part only of the first image.

Thus the invention provides to implement two cylinders or ring portions rotatable around two axes crossing at a center from which center radiation is generated forming a non-zero angle between them (preferably equal to 90°), those rotatable elements being formed from open parts and from portions opaque to the radiation such that the crossing of parts of those elements of the same nature define either a non-illuminating zone within a large illuminated zone, or an illuminated zone within a large non-illuminated zone, those elements being actuated in rotation by stepper motors of which the elementary steps have angular amplitudes which are sub-multiples of the amplitude of the parts which cross.

In the context of the invention, a step of a motor is referred to herein as an "elementary step" when that step is the smallest, taken with any reduction gearing, that such motor is configured to operate according to its supply mode; thus when that supply is made pole by pole, the elementary step is equal to one step of the motor, whereas, if the supply is made two poles by two poles, the elementary step is a half-step of the motor; when, in a measurement cycle, it is provided always to apply several pulses to such a motor, the elementary step may then be understood as being the step to which such a number of pulses corresponds. The angular step through which an element actuated by such a motor turns when the latter turns by such an elementary step is called "elementary angular step" or "scanning elementary step".

Preferably, one of the ring portions forms part of a complete ring of which the actuation is provided by a stepper motor designed to be able to rotate that ring in the same rotational direction; by way of variant, each of the portions may turn in one direction, then the other to return to a configuration of start of scanning.

There are thus two cases, depending on whether the elements that cross are open parts or parts opaque to radiation, with an "illumination beam" which is, either a locally increased illumination beam, or a locally neutralized illumination beam.

Thus, according to a first definition of the invention, the latter provides a scanning illuminating device comprising an illumination source defining an emission center, a collimation element delimiting a sector of illumination from the center in which the emitted radiation is substantially homogenous, at least one cylindrical ring portion centered on the source and rotatable about a first axis passing through the emission center, that cylindrical ring portion comprising a slit having an angular amplitude $\alpha$ surrounded by two portions transparent to radiation each having an angular amplitude at minimum equal to that of the illumination sector delimited by the collimation element, a cylinder portion centered on the source and rotatable, within a given travel, around a second axis passing through the emission center and forming a non-zero angle relative to the first axis, that cylinder portion comprising a slit parallel to the second rotational axis having an angular amplitude $\beta$ surrounded by two portions transparent to the radiation each having an angular amplitude at minimum equal to that of the illumination sector delimited by the collimation element, a first device for stepwise actuation of the rotation of the cylindrical ring portion defining an elementary angular step $\alpha\alpha$ which is a sub-multiple of the angular amplitude $\alpha$ of said slit of that cylindrical ring portion such that there is an integer N1 different from 1 meeting the condition $\alpha=N1\cdot\alpha\alpha$, and a device for stepwise actuation of the rotation of the cylindrical ring portion defining an elementary angular step $\beta\beta$ which is a sub-multiple of the amplitude $\beta$ of the slit of that cylinder portion such that there is an integer N2 different from 1 meeting the condition $\beta=N2\cdot\beta\beta$.

Particularly advantageously, the cylindrical ring portion is a cylindrical ring comprising a plurality of slits having said angular amplitude $\alpha$ and which are regularly distributed around its rotational axis and the first stepwise actuation device is designed to be able to actuate that ring in the same rotational direction.

According to the other definition referred to above (which inverses the role of the open parts and the slits of the aforementioned device, the "illumination beam" being a beam in which the lighting amplitude is locally reduced), the invention also provides a scanning illuminating device comprising an illumination source defining an emission center, a collimation element delimiting a sector of illumination from the center in which the emitted radiation is substantially homogenous, at least one cylindrical ring portion centered on the source and rotatable about a first axis passing through the emission center, that cylindrical ring portion comprising a portion opaque to the radiation and having an angular amplitude $\alpha$ surrounded by two portions transparent to the radiation each having an angular amplitude at minimum equal to that of the illumination sector delimited by the collimation element, a cylinder portion centered on the source and rotatable, within a given travel, around a second axis passing through the emission center and forming a non-zero angle relative to the first axis, that cylinder portion comprising a portion opaque to the radiation which is parallel to the second rotational axis and has an angular amplitude $\beta$ surrounded by two portions transparent to the radiation each having an angular amplitude at minimum equal to that of the illumination sector delimited by the collimation element, a first device for stepwise actuation of the rotation of the cylindrical ring portion defining an elementary angular step $\alpha\alpha$ which is a sub-multiple of the angular amplitude $\alpha$ such that there is an integer N1 different from 1 meeting the condition $\alpha=N1\cdot\alpha\alpha$, and a device for stepwise actuation of the rotation of the cylindrical ring portion defining an elementary angular step $\beta\beta$ which is a sub-multiple of the amplitude $\beta$ such that there is an integer N2 different from 1 meeting the condition $\beta=N2\cdot\beta\beta$.

Particularly advantageously, the cylindrical ring portion is a cylindrical ring comprising a plurality of slits regularly distributed around its rotational axis and separated by opaque portions having said angular amplitude $\alpha$ and the first stepwise actuation device is designed to be able to actuate that cylindrical ring in the same rotational direction.

It can be appreciated that such a scanning illuminating device, called modulator below, is compact in that the movements of the beam are made in two transverse scanning directions in a volume scarcely greater than that of a known chopper wheel. Furthermore, the fact that the movements are actuated by stepper motors enables the taking of images of an object so illuminated to be made at a very specific frequency, to which corresponds a very specific angular measurement step (which is the angular step of rotation of one or other of the rotary elements between two instances of image taking). The taking of images may be carried out outside the movements of those motors if those movements are sufficiently slow; as a variant, if the motors do not completely stop between two successive measurement steps, the images so captured between those two measurement steps may be subjected to blur correction processing, as is known, in particular, in the field of tomography.

The fact that the elementary steps of these stepper motors are such that the beams emitted for two positions neighboring by an elementary step have parts in common advantageously makes it possible to vary the illumination in several ways depending on whether the motors are actuated elementary step by elementary step (a measurement step then corresponds to an elementary step), or multiple steps by multiple steps (a measurement step then having the value of several elementary steps), while enabling the scanning to be applied to the whole of the object, whatever the ways chosen. It can be understood that the elementary scanning steps contribute to determining the maximum spatial resolution which can be attained by an imaging device comprising such a modulator, without that resolution being imposed by the dimensions of the illumination beam, which makes it possible to increase the use of the stream generated by the radiation source, or on the contrary to reduce the power of that radiation source.

Such a modulator may be considered as being dynamic in that the spatial resolution may be chosen and modified according to need for the same structural configuration.

According to preferred features of the invention:
  The angular amplitudes $\alpha$ and $\beta$ are equal and the integers N1 and N2 are equal; this simplifies the geometry of the illumination beam as well as the later processing, within an imaging device.
  the integers N1 and N2 are both odd, which has the advantage of enabling the illumination beam to be centered on an elementary beam of which the angular amplitude would be that of a single elementary step; this arises from the mathematical formulae which are symmetrical, but even numbers are just as usable.
  the number of slits is comprised between 5 and 10 (this applying when the illumination beam is delimited by the slits and also when the opaque parts locally obscure the illumination beam); this corresponds to a reasonable number from a practical point of view.

The device contained in a casing of dimensions less than 50×50×50 cm³; this results in a good level of compactness, which enables the device to be portable by an operator without great difficulty.

The invention is furthermore directed to providing a scanning imaging device, using X-rays for example, in back-scatter or transmission, of which the spatial resolution of the back-scattered or transmitted image is not determined by the dimensions of the scanning beam and may, preferably, be adjusted according to the needs of the analysis without having to modify the structure of that device. It is also directed to enabling use of a significant part of the radiation emitted by the radiation source, therefore enabling the utilization of sources that are less powerful than the known solutions.

More particularly the invention further provides a scanning imaging device comprising an illuminating device of the aforementioned type, further comprising a reception zone of which the volume is configured to receive an object to image, and at least one unitary detector positioned relative to that reception zone such that its field of view can detect radiation back-scattered or transmitted by such an object subjected in that zone to scanning by a scanning beam emitted by the illuminating device, while being synchronized with the stepwise actuation devices of the illuminating device so as to perform detection operations between successive measurement steps of those actuation devices and provide a measurement of radiation received in its field of view for each measurement position of the scanning beam actuated by those stepwise actuation devices, those measurement steps having the value of one or more elementary steps.

It is to be noted that, according to need, the actuation devices may actuate scanning according to the aforesaid elementary steps, or according to larger measurement steps.

Preferably:
the unitary detector is designed to be able to supply radiation measurements for positions of cylinder portions in which the zones of those portions which have said amplitude α or β intercept at most only part of the illumination sector of the illuminating device.

The device comprises at least one detector of scattered radiation and at least one detector of transmitted radiation.

As is known, two different quantities may be distinguished with regard to the dimensions of such a unitary detector: the thickness which is in practice configured for the radiation to detect (the thicker it is, the more the radiation interacts with the sensitive material of the detector, and the more effective the detection) and the area presented to the radiation stream to measure. This area solely depends on the quantity of radiation to intercept, which quantity is linked to the temporal response of the scintillator in the case of photon counting (pile-ups should be avoided) and the counting capacity of the card (it must be possible to individually count two pulses separated by a very short time). In the case of integrator operation, the size of the detector will depend on the dynamics of the integrator that follows the detector.

The invention also provides a method of forming an image of an object situated in a reception zone, wherein:
a. the object is subjected to scanning by an illumination beam emitted by an illuminating device as defined above, measurement step by measurement step in each scanning direction, each measurement step of one of the actuation devices of that illuminating device having the value of one or more elementary steps of that actuation device, b. after each measurement step of one of the actuation devices of that illuminating device, a measurement is acquired of the quantity of radiation scattered (and/or transmitted) by the object subjected to the illumination beam at that time and that measurement is stored in a matrix of which the rows and the columns correspond to the respective positions of the actuation devices of the illuminating device, c. next the image of the object is reconstructed by deconvolution of said matrix containing said measurements by a matrix representing the illumination beam at that time.

Advantageously, the object is first subjected to scanning by an illumination beam emitted by the illuminating device with a measurement step equal to a number of elementary steps greater than 1, part of the object to analyze is selected within the reception zone and steps a to c are applied to that part only with a measurement step equal to said elementary step.

It can be understood that, to apply the aforesaid steps to part only of the object, it is possible to take radiation measurements only for some of the positions of the cylinder portion (which amounts to not taking measurements over the full amplitude possible, transversely to the second rotational axis; as regards the scanning actuated by the first stepwise actuation device, it may be chosen to take measurements only for some possible positions of a slit, or to choose back-and-forth actuation of such a stepwise device. Selective scanning of part only of an object is particularly easy when each stepwise actuation device actuates, in back-and-forth actuation, a single portion cylinder, in particular when the cylindrical ring 3 or 103 is reduced to a cylinder portion.

BRIEF DESCRIPTION OF THE DRAWING

Objects, features and advantages of the invention will appear from the following description, given by way of illustrative non-limiting example with reference to the accompanying drawings in which.

DETAILED DESCRIPTION

Figure 1:
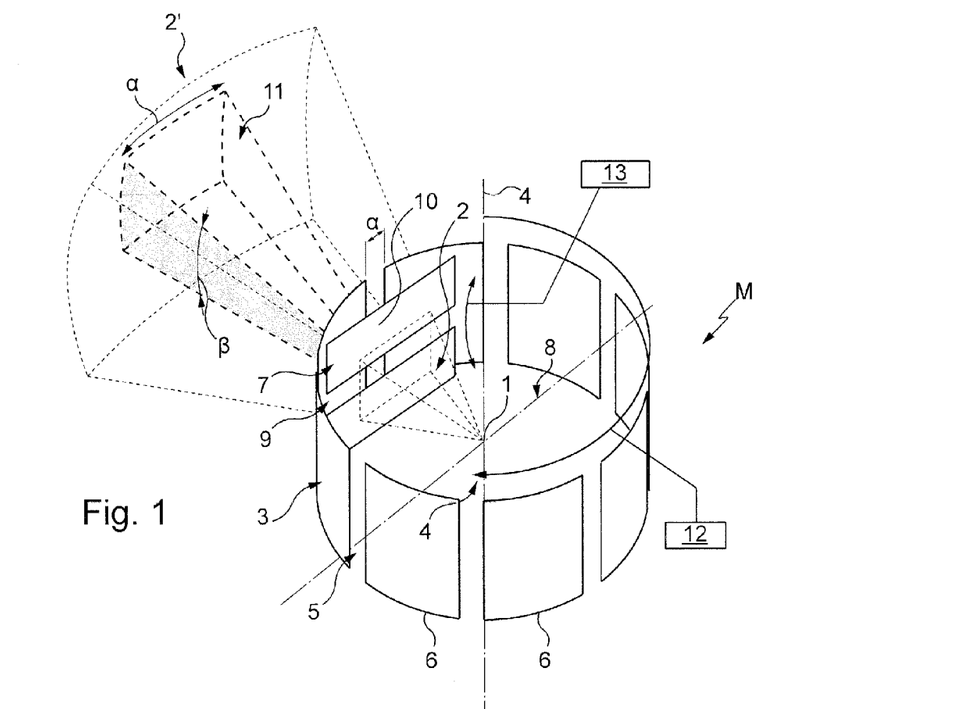
FIG. 1 is a synoptic diagram of an scanning illuminating device according to a first example embodiment in accordance with the invention.

FIG. 1 represents a scanning illuminating device, called radiation modulator, according to first embodiment of the invention.

This modulator, denoted M overall, comprises a radiation source 1 assumed to be localized and thus situated at a point, which is designated by the reference 1. This radiation source may be a continuous source emitting a constant stream of photons or else a pulsed source emitting a succession of identical pulses at a determined frequency; in this second case, the time between two successive pulses is sufficiently small relative to the changes in configuration of the modulator (see below) for the average stream of radiation to be considered as practically constant.

It is around this point 1, called emission center, or just center, below, that the other elements constituting the modulator are disposed.

In a general manner, this modulator is operative to move, in front of the source, alternations of materials that are absorbent and non-absorbent of the radiation from the source in order to successively illuminate determined zones of space so as to form a beam providing scanning in two directions that are transverse to each other and transverse to the direction of the scanning beam.

This modulator comprises a static primary collimator suitable for giving the beam emitted by the source 1 a given form and amplitude; the beam so collimated is designated by reference 2 which thus indirectly designates that primary collimator; the extension of this beam to the outside of the modulator is designated by reference 2'. It can be understood that this collimator delimits the zone of space (it is an angular sector starting at the source 1) in which the radiation from the primary source may, by virtue of the other elements of the modulator, be projected outside the modulator, and in which must be situated an object to image. In the represented example, this angular sector is pyramidal but may, as a variant, be conical, or even have a more complex form, for example hexagonal, or even a form with several lobes.

This angular sector defines the angular field in which the modulator can provide illumination by scanning.

Around the source and the collimator there is disposed a cylindrical ring designated by the reference 3. This ring is centered on an axis 4 around which it is rotatable; this axis, here vertical, passes via the source 1, that is to say the center of the modulator. This ring comprises a plurality of slits 5, in practice parallel to its axis; these slits, 8 in number here, are all identical and their angular spacing is regular (that is to say that the angular spaces, or intervals, between two successive slits are identical, whatever the slits considered). The function of these slits is to allow to pass a fraction of the radiation 2 transmitted by the collimator when they are positioned in front of it; on the other hand, the closed zones 6 situated between those slits are dimensioned such that the radiation transmitted by the collimator can be fully blocked, and thus stopped, by each of those closed zones. These full zones, which are opaque to the radiation, have an angular amplitude at minimum equal to the angular amplitude, around the axis 4, of the illumination sector delimited by the collimation element. These slits have angular amplitudes, measured relative to the center 1, which are the same, denoted $\alpha$.

The modulator further comprises a portion 7 of a second cylinder, of axis 8 passing by the source 1, making a non-zero angle, preferably equal to 90°, with the axis of the cylindrical ring 3. This portion 7 is also rotatable around its axis 8. I comprises a single slit 9, in practice parallel to that axis 8; its angular amplitude from the center 1 is denoted $\beta$. This slit, conjointly with the slits 5, is also operative to allow passage of a fraction of the radiation 2 transmitted by the collimator when it is positioned in front of the latter; it can be understood in fact that each of the slits 5 may delimit, with the slit 9 an aperture delimiting, according to each of the axes, a fraction of the collimated beam that is permitted, at a given instant, to illuminate a fraction of the external space. As for the closed portions 6 of the cylindrical ring 3, the closed portions 10 situated on respective opposite sides of the slit 9, which are opaque to the radiation, have a sufficient angular amplitude to enable the entirety of the collimated beam 2 to be blocked, and thus have an angular amplitude at least equal to the angular amplitude, around the axis 8, of the illumination sector delimited by the collimation element.

In the configuration represented in FIG. 1, one of the slits 5 delimits with the slit 9 an illumination beam designated by reference 11. For reasons of legibility, the dimensions of the latter have been exaggerated in FIG. 1 relative to the angular dimensions of the aperture formed conjointly by the slit 9 and one of the slits 5; as a matter of fact, its amplitude in width (perpendicular to the slits 5) has the value $\alpha$ while its amplitude in height (perpendicular to the slit 9) has the value $\beta$.

By way of example, the beam represents $\frac{1}{16}$th of the zone covered by the collimator $(9°/36°)^2$.

Advantageously these angular amplitudes $\alpha$ and $\beta$ are equal to each other.

The cylinder portion 7 is here situated within the volume of the cylindrical ring, but may as a variant be situated outside it.

The modulator further comprises stepper motors enabling the ring 3 and the portion 7 to be moved in their respective movements. The fact that these motors are of stepper type means that they are configured to incrementally move the ring and respectively the cylinder. The concept of stepper motors here includes the reduction gearing with which they are usually provided.

The arrow situated above the cylindrical ring 3 of FIG. 1 designates a constant direction of movement (here clockwise), while the arrow associated with the portion 7 is double, which means that portion can move in either direction around its axis 8, within a given angular travel. The stepper motor associated with the movement of the ring is shown diagrammatically under the reference 12, while that associated with the movement of the cylinder portion is shown diagrammatically under the reference 13.

The constancy of the direction of scanning by the cylindrical ring 3 is rendered possible by the regular distribution of the slits 5 and of the closed zones 6; is will be understood below that, as a variant, it suffices for the cylindrical ring to comprise a single slit 5 (or be reduced to one cylindrical ring portion) if the associated stepper motor 12 can act in both directions (one direction for the scanning and the opposite direction to return to starting configuration); however, as will be apparent below, it is much simpler for the cylindrical ring to be only moved in one direction, and this enables faster scanning. Of course, both types of actuation (single direction, and back and forth, according to need).

The stepper motors 12 and 13 are actuated so as to be able to act in synchronized manner on the cylindrical ring 3 and the cylinder portion 7. In particular, the stepper motor 13 actuating the cylinder portion 7 makes that cylinder portion advance by one measurement step (angular separation between two configurations in which an image is taken—as will be detailed later, this measurement step may have the value of one elementary step or several of those elementary steps) when the stepper motor 12 actuating the cylindrical ring 3 turns through an angle corresponding to the angular amplitude combined with a closed portion 6 and a slit 5 (the ring is formed from a plurality of patterns, each pattern comprising a slit and a closed part). In other words, the rotation of the motor 12 necessary to bring a slit into the same angular position as the preceding slit corresponds to a whole number of its elementary steps.

Similarly, the angular amplitude of the slits 5 corresponds to a whole number of elementary steps of the motor 12.

Similarly, the angular amplitude of the single slit 9 advantageously corresponds to a whole number of elementary steps of the motor 13.

To be precise, for a given position of the cylinder portion, scanning parallel to the axis thereof is provided by moving a slit, measurement step by measurement step, from on to the other of the sides of the collimated beam; next, the scanning continues in the same manner, by virtue of an adjacent slit, for another position of the motor after the movement of a new measurement step.

It is important to note that, according to the invention, stepper motors have elementary steps which correspond to angular amplitudes which are sub-multiples of the angular amplitudes of the slits 5 or 9.

Thus, if $\alpha\alpha$ is the elementary angular amplitude of an elementary step of the motor 12, there is an integer N1 different from 1 such that $\alpha=N1\cdot\alpha\alpha$.

Similarly, if $\beta\beta$ is the elementary angular amplitude of an elementary step of the motor 13, there is an integer N2 different from 1 such that $\beta=N2\cdot\beta\beta$.

The elementary steps of angular rotation of the ring 3 and of the cylinder portion 7 are advantageously equal ($\alpha\alpha=\beta\beta$), which makes it possible to ensure scanning of the same fineness in both scanning directions. On a subsidiary basis, this facilitates the implementation of identical motors for both scanning directions.

Similarly, it is advantageous to give equal angular amplitudes, $\alpha=\beta$, to the slits (hence a square shape of the sections of the apertures thus conjointly delimited). When $\alpha\alpha=\beta\beta$, this amounts to saying that N1=N2.

It may be noted that the illumination beam leaving the modulator, that is to say passing through slits of the ring and of the cylinder portion, maintain a shape and dimensions that are identical when it moves angularly: this outgoing radiation beam is named pencil in the following portion of text.

Figure 2:
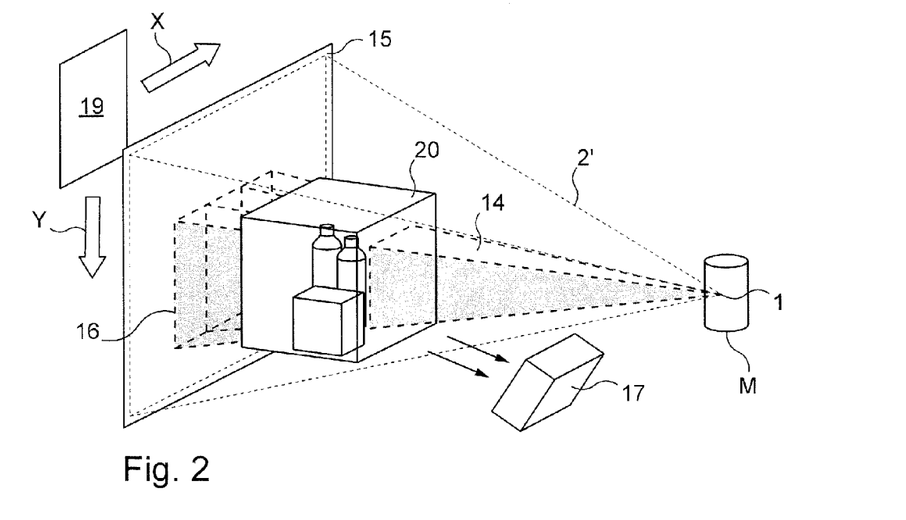
FIG. 2 is a synoptic diagram of an imaging device implementing the modulator of FIG. 1.

FIG. 2 represents an example of use of the modulator of FIG. 1 to produce a device for back-scattered and/or transmitted imaging. The modulator M is illustrated diagrammatically therein in the form of a small cylinder much smaller than in FIG. 1, for reasons of legibility.

An object 20 to image (or the part which it is wished to image within an object) is placed inside the field 2' in which the modulator is capable of providing illumination by scanning. It may be understood that this object to image, that is to say to analyze by means of the chosen radiation, is often a container the single or multiple content of which it is desired to identify; it is represented diagrammatically here by a cube in which several items are hidden. The cube here occupies practically the whole of the volume of a reception zone within which an object must be located to be able to be analyzed; the shape of this reception zone is defined by the shape of the primary collimator. Below, reference 20 will designate in the same way that reception zone and the object to image which is situated therein.

As was explained with regard to FIG. 1, the modulator makes it possible to scan the object 20 to analyze with a radiation pencil 11 delimited by the crossing of one of the slits 5 of the ring and the slit 9 of the second cylinder. It is to be recalled that the radiation pencil is represented exaggeratedly large; it is designated by reference 14 when it is in central position. The projection of that radiation pencil into a plane 15 situated behind the object is referenced 16. According to an aspect of the invention, in projection into a transverse plane passing through the object, the radiation pencil of greater dimension than the spatial resolution sought in the back-scattered (or transmitted) image since the spatial resolution does not depend on the size of the radiation pencil but it depends on the step of movement thereof between two measurements, that is to say between two instances of image taking (hence the concept of measurement step). It is thus possible, according to the invention, to use a quite large radiation pencil to pass sufficient radiation and improve the signal-to-noise ratio at the detector. Reference 17 designates a unitary detector which detects the radiation back-scattered by the object for each illumination position of the radiation pencil coming from the source and selected by the modulator. The transmitted image (the same reasoning applies to the back-scattered image) is reconstituted from the set of successive recordings as described below.

The unitary detector 17 serving to detect the image back-scattered by the object 20 is advantageously complemented by a unitary detector of large size in order to detect the radiation transmitted through the object for each position of the pencil radiation beam and use that information, following the same principle as for a back-scattered image, to reconstruct an image from the radiation transmitted by the object as a complement to the back-scattered image. As a variant, it may be chosen to form only a transmitted radiation image. This unitary detector for transmitted image detection may be constituted by the plane 15 represented in FIG. 2.

The starting position for a scanning cycle corresponds to positions of the ring and of the cylinder portion such that the trace on the plane 15 of the angular sector delimited by a slit 5 and a slit 9 (the term "pattern" is used subsequently) is located outside the analysis zone; this starting position is designated by the reference 19. That is to say that, a minima, the outer limit of the pattern 19 is tangential to the outer limit of the trace on the plane 15 of the analysis zone 2'. The scanning is terminated when the pattern has traversed stepwise the whole analysis zone and has arrived at the opposite outer limit of that zone. It is to be noted that, in the case represented in which the starting position 19 is tangential to the analysis zone, there is no pencil radiation beam since the aperture delimited by one of the slits 5 and the slit 9 is outside the collimated beam 2'. The same will apply at the time of the first scan in a direction X or Y (see the arrows in FIG. 2), for the extreme positions of the following scans and at the time of the last scan. This is why it may be preferable for the starting position to correspond to a position in which the trace 19 is superposed on the trace of the analysis zone over an amplitude corresponding to one motor step in each of the directions.

At the limit it is possible to start with a motor step in the zone 2' knowing that the preceding row will be at zero. In reality that first row will not be zero but will contain background noise above all. By shifting several steps, the size of the reconstructed image will be the same number of steps smaller. Thus by starting at the edge, the entirety of the zone delimited by the primary collimator is taken advantage of.

The scattered radiation measurement (the reasoning is the same for the transmitted radiation) received by the unitary detector 17 is synchronized with the stepper motors. After each movement of one of the two cylinders (that is to say after each measurement step) a measurement of scattered radiation arriving on the detector is started and that measurement is stopped at the next movement of one of the two cylinders. The detector measures the quantity of radiation it receives, over the entirety of its field of view, either by counting the photons (weak radiation stream), or by integration of the radiation (high radiation stream). The choice of the detection mode depends on the activity of the source, on the characteristics of the modulator and on the geometry of the device. The measurements are stored row by row in correspondence with the X-Y scanning of the zone illuminated by the radiation pencil beam. The measurements end when the entire zone delimited by the primary collimator has been scanned. The set of measurements constitutes a matrix corresponding to the convolution product of the back-scattered image of the object with the intensity and the shape of the projection of the radiation pencil beam in the plane of the object. An operation of deconvolution of that matrix enables the back-scattered image to be reconstructed. The matrix corresponding to the shape and the intensity of the projected pencil beam may be computed based on the knowledge of the width of the slits of the modulator and of the acquisition geometry. It may also be identified experimentally in a laboratory using an imager.

The scanning step, between two measurements, defines the pixel size of the image. The spatial resolution of that image is thus fixed by the size of the movement step of the radiation pencil beam in movements by the motors. This imaging device thus makes it possible to choose, and thus to modify, the spatial resolution with which the object is analyzed without modification either of the device itself, or of its installation in relation to the object. It is thus possible to rapidly make a first image with low resolution (with a coarse scanning step, with a measurement step equal to several elementary steps) to determine a zone of interest which will then be inspected with a finer resolution (reduced scanning step, that is to say with a measurement step equal to a smaller number of elementary steps, possibly equal to 1) for example.

same in both directions; the number of elementary steps contained in one side of that trace is denoted h. In other words, h is the number of positions of the beam, in each scanning direction, for which the same elementary zone of the object interacts with the scanning beam.

Figure 3:
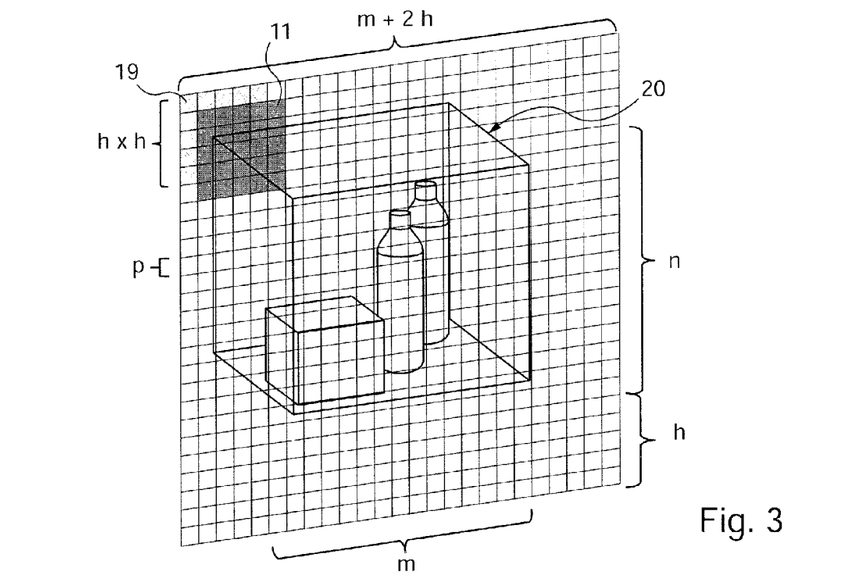
FIG. 3 is a diagram showing the constitution of a matrix for acquiring measurements made on an object subjected to scanning by the modulator of FIG. 1.

In the case defined above in which the scanning is carried out with extreme positions where the aperture defined by the slits is tangential, without overlap, to the trace of the analysis zone, the total zone of scrutiny represented on that FIG. 3 is of width m+2 h and of height n+2 h if m and n are the numbers of elementary steps in width and in height to explore the analysis zone and thus the size of the reconstructed image.

After a first scan in the X direction (without illumination), the second scan, after an elementary step p downward, makes the beam 11 circulate in such a way as to intercept the collimated beam, such that it provides an illumination of the object, even though this is with dimensions different from those which that beam would have when the apertures delimited by the slits 5 and 9 are fully contained in the collimated beam.

The total number of measurement steps (or scrutinizing steps) in this case is (m+h)·(n+h).

Let X (i,j) denote the matrix representing the back-scattered image which it is sought to reconstruct. At each elementary step, if the numbers of elementary steps made by the actuation devices are denoted by k and i, the quantity $M_{kl}$ measured by the detector is proportional to the sum (on the rows and columns) of the product (multiplication term by term) of the matrix X by the matrix H representing the shape and the intensity of the radiation pencil beam projected into the plane of the object.

The principle of the construction of a measurement acquisition matrix is illustrated diagrammatically in FIG. 3. This diagram serves to illustrate the fact that the scanning zone may be cut up virtually into pixels which correspond to a movement step, here an elementary step. However, since each detector is of unitary type, it provides a single measurement at a time.

As a matter of fact all the information coming from the detector is used; its measurement constitutes an element of the measurement matrix, for a position of the beam.

Since, as explained above, the angular amplitudes of the radiation pencil beam are multiples of those elementary steps, the trace of such a pencil beam on a zone of the object is delimited by a rectangle, or even by a square in the case considered here in which the angular amplitudes are the Object X Multiplication Term by Term Pencil Beam H Written otherwise, for a pencil beam H of size h×h with h=2N+1

$$M_{kl} = \sum_{j=-N}^{N} \sum_{i=-N}^{N} X(k-i, l-j).H(i,j)$$

Which, in the context of the distributions, corresponds to the convolution product of X by H.

$M_{kl} = (X*H)(k,l)$ where * is the convolution product

Mathematical definition of the convolution according to the functions:

$$(f*g)(x,y)=\int_{-\infty}^{\infty}\int_{-\infty}^{\infty}f(x-t,y-u)\cdot g(t,u)\cdot dt\cdot du=\int_{-\infty}^{\infty}\int_{-\infty}^{\infty}f(t,u)\cdot g(x-t,y-u)\cdot dt\cdot du=(g*f)(x,y)$$

Which for the entirety of the scanning, gives the convolution product between the object X and the pencil beam H.

$$\begin{pmatrix} x_{11} & x_{12} & x_{13} & x_{14} & \cdots & x_{1j} & \cdots & x_{1n} \\ x_{21} & & & & & & & \\ x_{31} & & & & & & & \\ \vdots & & & & & & & \\ x_{i1} & \cdots & \cdots & \cdots & x_{ij} & \cdots & \cdots & x_{in} \\ \vdots & & & & & & & \\ x_{m1} & \cdots & \cdots & \cdots & \cdots & \cdots & \cdots & x_{mn} \end{pmatrix}$$
Object X, Dimensions $m \times n$ $$* \begin{pmatrix} a & b & c & d \\ e & & & \\ f & g & h & i \\ j & & & \\ k & l & m & n \end{pmatrix}$$
pencil beam H, $h \times h$ $$= \begin{pmatrix} M_{11} & M_{12} & M_{13} & M_{14} & \cdots & M_{1l} & \cdots & M_{1q} \\ M_{21} & & & & & & & \\ M_{31} & & & & & & & \\ \vdots & & & & & & & \\ M_{k1} & \cdots & \cdots & \cdots & M_{kl} & \cdots & \cdots & M_{kq} \\ \vdots & & & & & & & \\ M_{p1} & \cdots & \cdots & \cdots & \cdots & \cdots & \cdots & M_{pq} \end{pmatrix}$$
measurements M, $(m+h) \times (n+h)$ Nota bene: it is not mandatory for the matrices to be square. The pencil beam may have any suitable dimensions. A pencil beam of dimension 1 will be equivalent to scanning by a very fine beam and the matrix of the measurements will directly be the image of the object.

It may thus be understood that, on the same object, first coarse scanning may be carried out, with an enlarged measurement step, for example equal to h elementary steps in at least one direction (with a processing operation indicated at the preceding paragraph for the pencil beam of size equal to the elementary step), then fine scanning scrutinizing the object with the minimum step, that is to say the elementary step.

The object X may be reconstructed by several mathematical methods based on the measurement matrix M and the pencil beam matrix H. This reconstruction may be carried out by the use of an algorithm, a matrix inversion method or for instance by taking advantage of the properties of Fourier transforms.

$$f * g = F^{-1}[F(f).F(g)] \quad \begin{array}{l} F \quad \text{Fourier transformation} \\ F^{-1} \quad \text{inverse Fourier transformation} \end{array}$$

To retrieve the object X based on the measurement M and the pencil beam H using the Fourier transformations:

$$X = F^{-1}[F(M)/F(H)] \text{ division term by term}$$

It should be noted that the method of reconstructing the image does not make use of any source/object/detector size. The image is sharp everywhere.

Corrections may be made to the reconstructed image (they are within the capability of the person skilled in the art):

in principle, the source must emit a constant quantity of radiation per unit time for the duration of the scanning. If this is not the case, correction of the measurements may be made based on monitoring of the source, it is possible for the spatial distribution of the intensity of the radiation emitted by the source inside the analysis zone not to be uniform. For example, the source may present an emission lobe. It will be possible for this non-uniformity to be the subject of correction of the reconstructed image provided measurement thereof has been made in advance, the geometry of the mechanical system is such that the projection of the radiation pencil beam is regular over a spherical dome. As the image of the object is reconstructed in a plane, it is possible to perform geometric corrections at the time of the reconstruction of the image in order to take into account that distortion. Possible blur of the images taken between two measurement steps, if there is no full stoppage of the motor considered, may be corrected by means of processing which is known per se in the field of tomography.

In order to improve the signal-to-noise ratio of the reconstructed image, it is possible to add other unitary detectors (positioned outside the emission zone of the modulator) which will simultaneously collect the scattered radiation reaching each of them during scanning. The position of these detectors is not involved in the reconstruction of the image, their putting in place is thus very fast and does not require painstaking adjustment. The advantage of using several detectors and their judicious disposition is also to limit the zones of shadow due to the masking by each other of the different parts of the object inspected. Lastly this disposition, by reconstruction of the individual images coming from each detector and by combination between them, gives access to the depth of the object inspected by using the principles implemented in photogrammetry.

Figure 4:
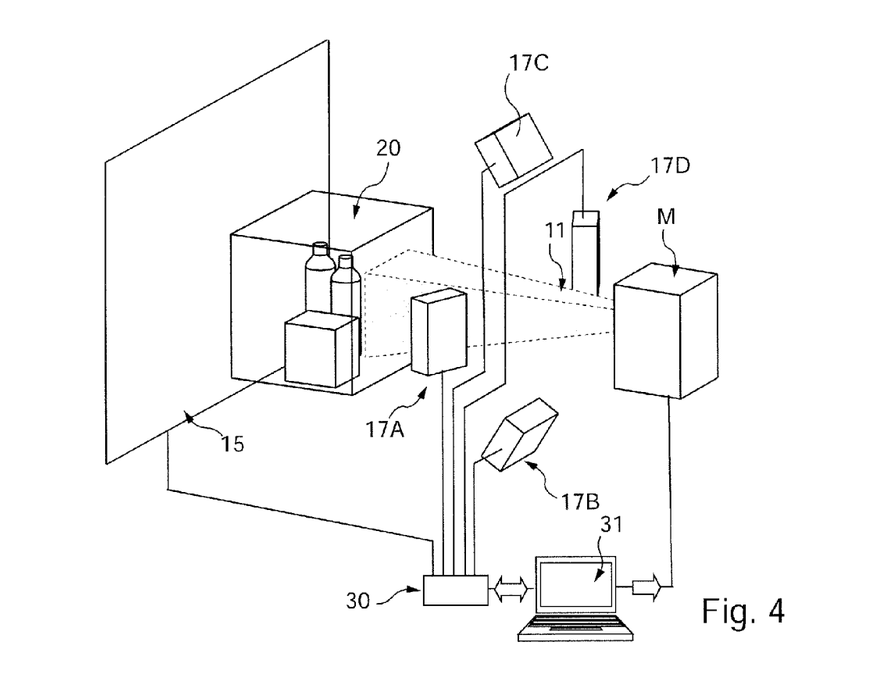
FIG. 4 is a diagram showing the constitution of another imaging integrating the modulator of FIG. 1.

FIG. 4 represents a complete device for back-scattered and transmitted imaging with a modulator M (including a radiation source) which generates a radiation pencil beam configured to be moved in two directions, several unitary detectors 17A, 17B, 17C and 17D measuring the radiation scattered by the object 20, a unitary detector 15 measuring the radiation transmitted through the object, electronics 30 for acquiring signals from the aforesaid detectors, and a system 31 for actuation and control which governs the stepper motors 12 and 13 of the modulator, synchronizes the detectors with the motors, and processes the signals to reconstruct the back-scattered and transmitted images.

An advantage of choosing values N1 and N2 equal to odd integers is that, when each measurement is made, the pencil beam is centered on a given pixel. Such a case is envisioned above, which has the advantage of a certain symmetry of the matrices; but the case of even values is just as possible, by modifying the matrices above.

When it is wished to be able to perform scanning with several different measurement steps, it has been indicated that there is at least the possibility of carrying out coarse scanning with a measurement step equal to the angular amplitude of the pencil beam in the direction considered (that is to say equal to N1 or N2 times the elementary step).

When it is wished to be able to perform, furthermore, scanning with an intermediate measurement step, it is recommended that this intermediate measurement step also be a sub-multiple of the angular amplitude of the pencil beam, which means that the integers N1 and N2 are advantageously numbers which are not prime, but products of smaller integers. It can be understood that if N1 and N2 (for which it has been stated that there is an advantage for them to be equal) are products of different integers, each of these integers then enables scanning at intermediate measurement step while following calculations easily deduced from those indicated above; by way of example, values N1=N2=5 enable scanning operations at measurement steps of 5 (coarse scanning) and of 1 (fine scanning), and values N1=N2=15 enable scanning operations at measurement steps of 15 (very coarse scanning), of 5 and of 3 (intermediate scanning operations) and of 1 (fine scanning).

Figure 5:
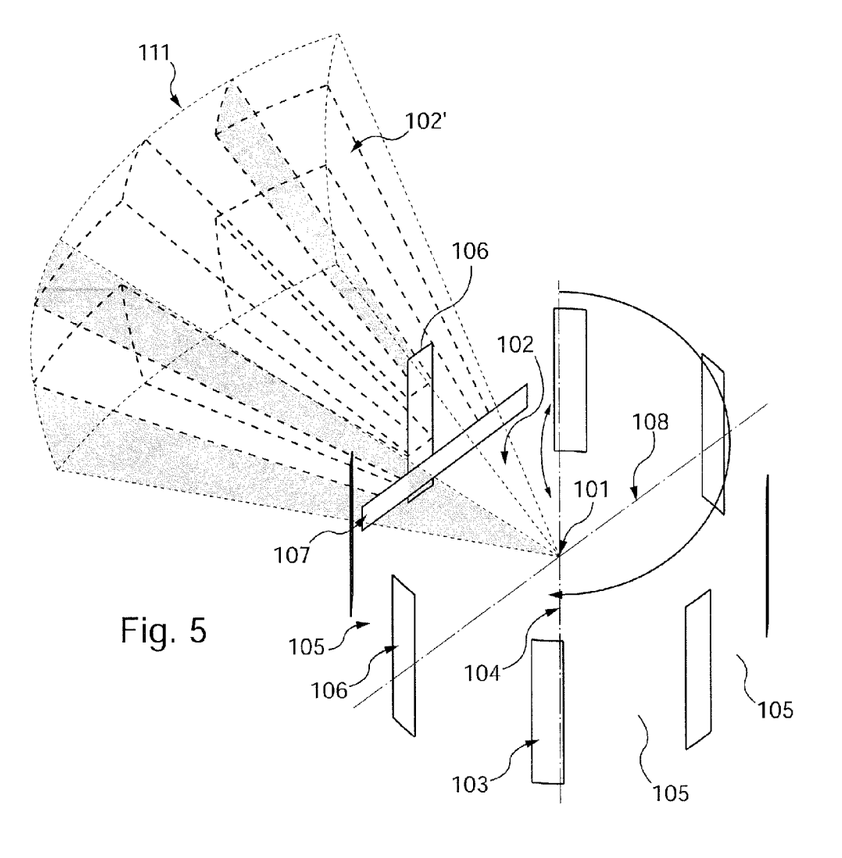
FIG. 5 is a diagram of a variant embodiment of the modulator of FIG. 1, implementing an inverse principle.

FIG. 5 represents a variant embodiment for a modulator in accordance with the invention, distinguished from the configuration of FIG. 1 by the fact that the width of the slits made in the cylinders at the point of inverting the closed and open parts of the ring and of the cylinder portion of the modulator M is very significantly increased. The parts similar to those of FIG. 1 are designated by reference signs which may be derived from those of FIG. 1 by increasing by the number 100; thus the center is denoted 101, the rotational axes 104 and 108; however, the cylinder portion is limited to a single closed part 107, of width similar to that of the closed parts 106 alternating with spaces 105 within the cylindrical ring 103. Through analogy with the above, the ring portion 106, which is opaque to the radiation, is delimited by two portions 105 transparent to the radiation, each having an angular amplitude at minimum equal to the illumination sector 102 delimited by the collimation element around the first axis; similarly the portion 107 opaque to the radiation is delimited by two portions transparent to the radiation each having an annular amplitude at minimum equal to the illumination sector 102 delimited by the collimation element around the second axis. The radiation pencil beam occupies any space 102' delimited by the primary collimator with a cross-shaped shadow 111 moving during the scanning. Such a modulator may be integrated into a device for back-scattered and/or transmitted imaging (of which the other elements are similar to those described above), the construction of the images being carried out on the basis of radiation induced by the scanning of the shadow caused by the crossing of the closed parts. This disposition uses a greater portion of the radiation emitted by the source and thus makes it possible to improve the signal-to-noise ratio and/or to shorten the acquisition times.

Figure 6:
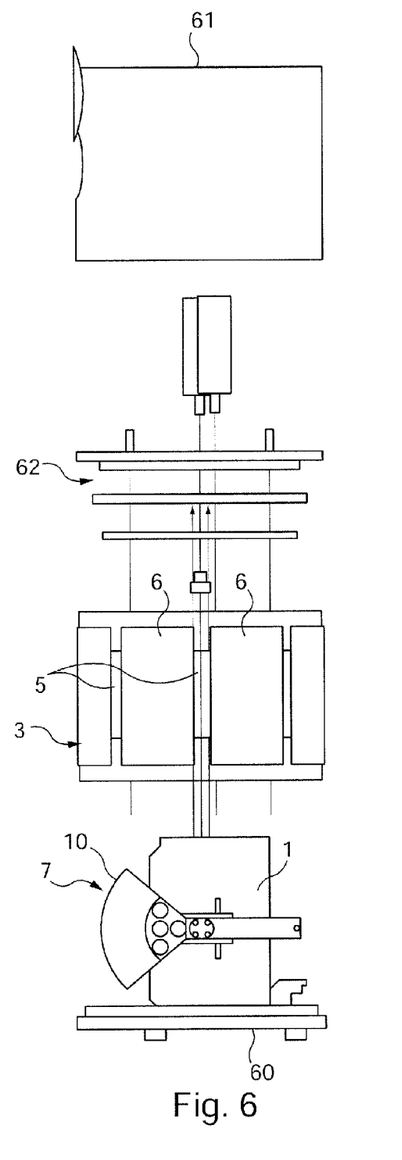
FIG. 6 is an exploded view of a modulator similar to that of FIG. 1, in side view.
Figure 7:
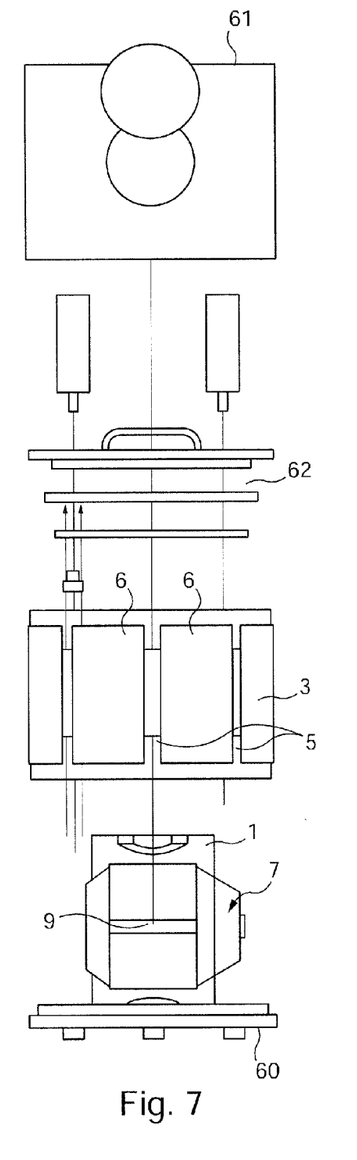
FIG. 7 is a front view.

FIGS. 6 and 7 show a radiation modulator produced for a commercially available portable X-ray source of 120 kV, 1 mA DC (CP120 from the company ICM). This source 1 is in practice contained in a cylindrical body; the latter is advantageously removable in relation to the rest of the modulator.

The primary collimation is of lead. It delimits a cone of 36° of which the vertex is the emission point of the generator (illuminated field of 65 cm diameter at 1 m from the center of the source). The collimator is not represented here per se.

The ring and the cylinder portion are provided with shutters 6 and 10 of tantalum of 3 mm thickness. The closed parts of the first cylinder cover an angle of 36°, the slits 5 and 9 each cover 9°. This disposition leads to eight slits on the cylindrical ring. The radiation pencil beam so formed by the crossing of the vertical and horizontal slits covers a square of 9°×9°, that is to say a sixteenth $(9°/36°)^2$ of the illuminated zone.

Two identical stepper motors (NEMA17, 0.9°) with integrated electronics of 200 steps per revolution actuate the two rotatable parts via reduction gearing with a 1/50 ratio. This configuration leads to movement of the slits of 0.036° per motor step. The scrutinized zone thus corresponds to 1000+ 250 motor steps (36°/0.036 and 9°/0.036). This makes it possible to reconstruct an image of 1000×1000 pixels. For a source/object distance of 1 m, the size of a pixel is 0.65×0.65 mm.

The motors are configurable in elementary steps of value ½ step, ¼, ⅛ steps, etc., which enables the acquisition of images of larger size thus of smaller resolution (0.018° in ½ step mode). For images of lower resolution, for example 500×500 (0.072°), two successive pulses are applied to the motors to make the slits advance between each measurement acquisition (the measurement step then having the value of two elementary steps).

These motors are actuated by programmable electronic cards which supply the signals for synchronization of the acquisitions and also count the pulses delivered by the detectors between two successive positions of the slits.

As in FIG. 1, the cylinder portion 7 is situated inside the volume of the cylindrical ring. It can however be understood that, as a variant, this cylinder portion may be situated outside that cylindrical ring.

The assembly is integrated within a casing comprising a support 60, a lateral wall 61 and covering elements 62.

By way of example, the diameter of the ring is 320 mm for a height of 270, which corresponds to a particularly compact device for scanning in two directions.

Figure 8:
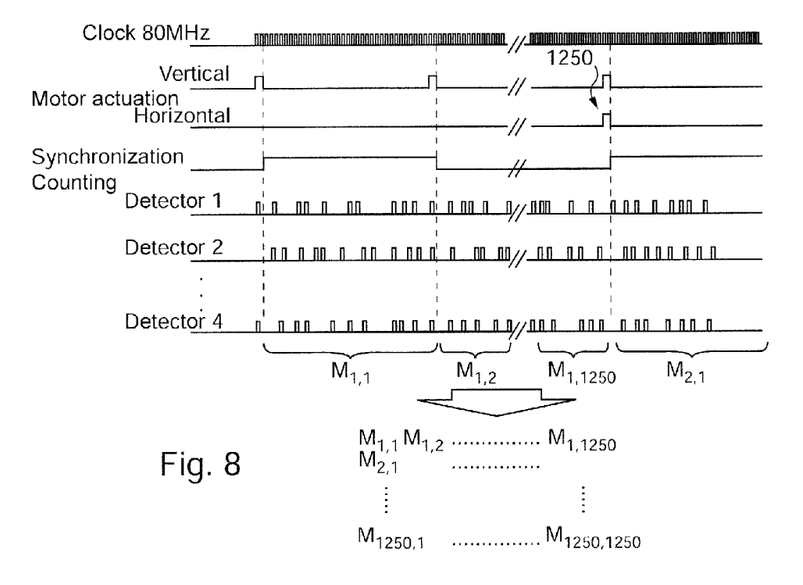
FIG. 8 is a timing diagram representing the operation of an imaging device in accordance with FIG. 4.

FIG. 8 is a timing diagram of the operation of such a modulator integrated into an imaging device comprising 4 detectors.

Based on a clock signal, here of 80 MHz, pulses of the vertical motor (that is to say of the motor which causes the rotation of the ring about the vertical axis) trigger rotational steps of the ring; however, one pulse is applied to the horizontal motor (that is to say to the motor which causes the rotation of the cylinder around the horizontal axis) after a number of pulses of the vertical motor corresponding to full scanning along a row (here over 1250 steps).

A synchronization signal alternates from one acquisition step to another: the measurements made after each movement of the vertical motor correspond to the values indicated above with regard to the matrix calculation enabling the image of the analyzed object to be reconstructed.

The acquisition of an image of 1000×1000 pixels of an object situated at 1 m from the source is carried out in 15 min. This corresponds to counting intervals of 576 μs and to a rotational speed of the ring of 10.4 revolutions per minute. An image of 200×200 pixels with the same signal-to-noise ratio is produced in 1 min. These acquisition times may be further reduced by increasing the number of detectors, the size of the scintillators and by using faster counter cards. To be precise, the more photons there are per pixel, the faster it is necessary to be able to count them.

Figure 9:
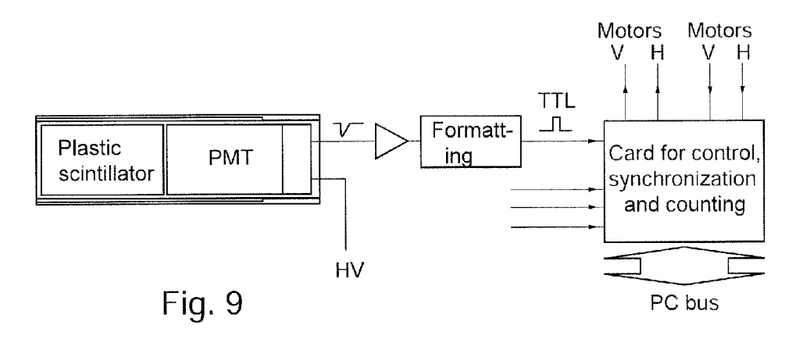
FIG. 9 is a synoptic diagram of a measurement acquisition chain.

FIG. 9 represents an example of a counter chain for the acquisition of the measurements; this counter chain comprises a fast plastic scintillator (the typical dimensions are a diameter of 50 millimeters for a height of 50 millimeters) coupled to a photomultiplier (PMT): the output signal is put into TTL format and is applied to a card for controlling synchronization and counting generating actuation signals for the motors.

It is to be noted that if, for a given analysis operation, it is chosen to use the actuation devices only with minimum steps which are multiples of the elementary steps, the comments made above regarding the elementary steps apply to the minimum steps; in other words, the concept of elementary step used above may be modified according to need, with the same structural configuration.

The system is in particular adapted to inspect objects of everyday life (suitcase, bag, cardboard package, etc.) upon the size of which depends the aperture of the primary collimator of the radiation source. An illuminated zone of the order of 50 cm seems to be a minimum. By placing the generator at 1 m from the object, this leads to a minimum angular aperture of the collimator of the order of 30°.

A reasonable maximum aperture is ≤90°, which leads to an illuminated field of 2 at a distance of 1 m; beyond, the illumination on the edges is less than 40% relative to the center (lobe of the radiation generator having a localized source).

The imaging principle used (in FIG. 1) means that at a time of the cycle the object is not illuminated. The closed parts of the modulator must therefore cover the aperture of the collimator. This advantageously gives a domain comprised between approximately 30 and 90° for the closed parts.

The slits between the closed parts must enable the passage of a significant part of the radiation. A minimum aperture of the order of 10° (field of 17 cm at 1 m) is desirable. The maximum aperture will be at most equal to the aperture of the collimation. Indeed, a greater aperture leads to acquiring more information than necessary to reconstruct the image. A large width of slit means a greater quantity of measurements to acquire and thus a longer time of scrutiny (to reconstruct an image m×n, the number of measurements required is (m+h)×(n+h) with h being the width of the beam. If the slits have the same width as the closed parts, it is necessary to acquire 4 times as many pixels of the image as it is desired to reconstruct. In a practical manner, the aperture of the slits may advantageously be limited to half the aperture of the closed parts to reduce the number of acquisitions (2.25 times the size of the image).

This leads preferably to choosing a domain comprised between approximately 10 and 45° for the slits.

The first choice to make is the size of the field to scrutinize. This requires the opening of the closed parts. The opening of the slits is a result of what has just been described (i.e. an aperture>10° and <½ the closed part). The regular distribution of those closed parts and slits, in the limit of the predefined apertures, on a cylinder, will set the possible values for those same apertures.

The implementation of a cylinder portion leaves a greater choice of possible apertures.

Examples of values of pairs of apertures for a distribution over a cylinder: all the pairs for which 360/(Slit+Closed)=integer operate with ≈30°≤closed≤90° et≈10° slit≤½ closed.

| Slit (°) | Closed part (°) | N patterns over a cylinder | Field illuminated at 1 m (m) |
|---|---|---|---|
| 9 | 27 | 10 | 0.48 |
| 10 | 30 | 9 | 0.54 |
| 9.3 | 30.7 | 9 | 0.55 |
| 15 | 30 | 8 | 0.54 |
| 15 | 45 | 6 | 0.83 |
| 30 | 60 | 4 | 1.15 |
| 18 | 72 | 4 | 1.45 |
| 30 | 90 | 3 | 2.00 |

The invention claimed is:

1. A scanning illuminating device comprising:
an illumination source defining an emission center;
a collimation element delimiting an illumination sector from the emission center in which emitted radiation is substantially homogenous;
at least one cylindrical ring portion centered on the illumination source and rotatable about a first axis passing through the emission center,
the least one cylindrical ring portion comprising a slit having an angular amplitude $\alpha$ surrounded by two portions transparent to radiation, each having an angular amplitude at minimum equal to that of the illumination sector;
a cylinder portion centered on the illumination source and rotatable, within a given travel, around a second axis passing through the emission center and forming a non-zero angle relative to the first axis,
the cylinder portion comprising a slit parallel to the second rotational axis having an angular amplitude $\beta$ surrounded by two portions transparent to the radiation, each having an angular amplitude at minimum equal to that of the illumination sector;
a first actuation device for stepwise actuation of rotation of the least one cylindrical ring portion defining an elementary angular step $\alpha\alpha$ that is a sub-multiple of the elementary angular amplitude $\alpha$, such that an integer N1 different from 1 and meeting the condition $\alpha = N1 \cdot \alpha\alpha$; and
a second actuation device for stepwise actuation of rotation of the ring portion defining an elementary angular step $\beta\beta$ that is a sub-multiple of the amplitude $\beta$ of the slit of the cylinder portion, such that an integer N2 different from 1 meets the condition $\beta = N2 \cdot \beta\beta$.

2. A device according to claim 1, wherein the least one cylindrical ring portion comprises is a cylindrical ring comprising a plurality of slits having the angular amplitude $\alpha$ and regularly distributed around the first axis and the first actuation device is configured to actuate the cylindrical ring in a same rotational direction.

3. A device according to claim 2, wherein the angular amplitudes $\alpha$ and $\beta$ are equal to each other and the integers N1 and N2 are equal.

4. A device according to claim 2, wherein the plurality of slits comprises 5 to 10 slits.

5. A device according to claim 1 contained in a casing of dimensions less than 50×50×50 cm³.

6. A scanning imaging device comprising:
a scanning illuminating device according to claim 1, the illuminating device emitting a scanning beam;
a reception zone having a volume configured to receive an object to image; and
at least one unitary detector positioned relative to the reception zone, such that a field of view of the at least one unitary detector can detect radiation backscattered or transmitted by the object subjected to scanning by the scanning beam, while being synchronized with the stepwise actuation devices of the illuminating device so as to perform detection operations between successive measurement steps of those actuation devices and provide a measurement of radiation received in its field of view for each measurement position of the scanning beam actuated by the stepwise actuation devices, the measurement comprising one or more elementary steps.

7. An imaging device according to claim 6, wherein the at least one unitary detector is configured to supply radiation measurements for positions of the cylinder portions in which the zones of those portions having said amplitude α or β intercept at most only part of the illumination sector of the illuminating device.

8. An imaging device according to claim 6, wherein the at least one unitary detector comprises at least one detector of scattered radiation and at least one detector of transmitted radiation.

9. A method of forming an image of an object situated in a reception zone, wherein
a. an object is subjected to scanning by an illumination beam emitted by an illuminating device according to claim 1, and carrying out a measurement step in each scanning direction, each measurement step of one of the actuation devices of the illuminating device comprising one or more elementary steps of the actuation device;
b. after each measurement step of one of the actuation devices of that illuminating device, a measurement is acquired of the quantity of radiation scattered and/or transmitted by the object subjected to the illumination beam at that time and that measurement is stored in a matrix of which the rows and the columns correspond to respective positions of the actuation devices of the illuminating device; and
c. the image of the object is reconstructed by deconvolution of the matrix containing the measurements by a matrix representing the illumination beam.

10. A method according to claim 9, wherein the object is first subjected to scanning by an illumination beam emitted by the illuminating device with a measurement step equal to a number of elementary steps greater than 1 for at least one of the stepwise actuation devices, part of the object to analyze is selected within the reception zone and steps a to c are applied to that part only with a measurement step equal to said elementary step.

11. A scanning illuminating device comprising:
an illumination source defining an emission center;
a collimation element delimiting illumination sector from the emission center in which the emitted radiation is substantially homogenous;
at least one cylindrical ring portion centered on the source and rotatable about a first axis passing through the emission center,
the cylindrical ring portion comprising an opaque portion opaque to the radiation and having an angular amplitude α surrounded by two portions transparent transparent to the radiation each having an angular amplitude at minimum equal to that of the illumination sector;
a cylinder portion centered on the source and rotatable, within a given travel, around a second axis passing through the emission center and forming a non-zero angle relative to the first axis,
the cylinder portion comprising opaque portion opaque to the radiation that is parallel to the second axis and has an angular amplitude β surrounded by two transparent portions transparent to the radiation each having an angular amplitude at minimum equal to that of the illumination sector delimited by the collimation element,
a first actuation device for stepwise actuation of the rotation of the cylindrical ring portion defining an elementary angular step αα that is a sub-multiple of the angular amplitude α, such that an integer N1 different from 1 meets the condition α=N1·αα; and
a second actuation device for stepwise actuation of the rotation of the cylindrical ring portion defining an elementary angular step ββ that is a sub-multiple of the amplitude β, such that an integer N2 different from 1 meets the condition β=N2·ββ.

12. A device according to claim 11, wherein the cylindrical ring portion comprises a cylindrical ring comprising a plurality of slits regularly distributed around the first axis and separated by opaque portions having the angular amplitude α and the first actuation device actuates the cylindrical ring in a same rotational direction.

13. A device according to claim 12 wherein the angular amplitudes α and β are equal to each other and the integers N1 and N2 are equal.

14. A device according to claim 12, wherein the plurality of slits comprise 5 to 5 slits.

15. A device according to claim 11 contained in a casing of dimensions less than 50×50×50 cm$^3$.

16. A scanning imaging device comprising:
an illuminating device according to claim 11, the illuminating device emitting a scanning beam;
a reception zone having a volume configured to receive an object to image; and
at least one unitary detector positioned relative to the reception zone, such that a field of view of the at least one unitary detector can detect radiation backscattered or transmitted by the object subjected to scanning by the scanning beam, while being synchronized with the stepwise actuation devices of the illuminating device so as to perform detection operations between successive measurement steps of those actuation devices and provide a measurement of radiation received in its field of view for each measurement position of the scanning beam actuated by the stepwise actuation devices, the measurement comprising one or more elementary steps.

17. An imaging device according to claim 16, wherein the at least one unitary detector is configured to supply radiation measurements for positions of the cylinder portions in which the zones of those portions having said amplitude α or β intercept at most only part of the illumination sector of the illuminating device.

18. An imaging device according to claim 16, wherein the at least one unitary detector comprises at least one detector of scattered radiation and at least one detector of transmitted radiation.

19. A method of forming an image of an object situated in a reception zone, wherein d. an object is subjected to scanning by an illumination beam emitted by an illuminating device according to claim 11, and carrying out a measurement step in each scanning direction, each measurement step of one of the actuation devices of the illuminating device comprising one or more elementary steps of the actuation device;

e. after each measurement step of one of the actuation devices of that illuminating device, a measurement is acquired of the quantity of radiation scattered and/or transmitted by the object subjected to the illumination beam at that time and that measurement is stored in a matrix of which the rows and the columns correspond to respective positions of the actuation devices of the illuminating device; and f. the image of the object is reconstructed by deconvolution of the matrix containing the measurements by a matrix representing the illumination beam.

20. A method according to claim 19, wherein the object is first subjected to scanning by an illumination beam emitted by the illuminating device with a measurement step equal to a number of elementary steps greater than 1 for at least one of the stepwise actuation devices, part of the object to analyze is selected within the reception zone and steps a to c are applied to that part only with a measurement step equal to said elementary step.

* * * * *